(12) United States Patent
Damm

(10) Patent No.: US 6,660,910 B1
(45) Date of Patent: Dec. 9, 2003

(54) SELECTION MARKER

(75) Inventor: Brigitte Damm, Bad Homburg (DE)

(73) Assignee: Syngenta Mogen B.V., Leiden (NL)

( * ) Notice: Subject to any disclaimer, the term of this patent is extended or adjusted under 35 U.S.C. 154(b) by 0 days.

(21) Appl. No.: 09/426,075

(22) Filed: Oct. 15, 1999

Related U.S. Application Data (63) Continuation of application No. PCT/EP98/02979, filed on Apr. 17, 1998.

(30) Foreign Application Priority Data

Apr. 18, 1997 (EP) .............................................. 97201140

(51) Int. Cl.[7] .......................... C12N 5/04; C12N 15/82; A01H 5/00
(52) U.S. Cl. ...................... 800/300; 800/278; 435/69.1; 435/468; 435/418; 435/419; 435/420; 435/431
(58) Field of Search ................................ 435/69.1, 69.8, 435/468, 469, 183, 418, 419, 420, 431, 252.2, 320.1; 800/278, 288, 292, 300, 320

(56) References Cited

U.S. PATENT DOCUMENTS 6,096,947 A * 8/2000 Jayne et al. ................. 800/300

FOREIGN PATENT DOCUMENTS

WO  WO 98/30701  7/1998

OTHER PUBLICATIONS

Maier–Greiner et al. Herbicide Resistance in Plants through the Degradation of the Phytotoxin to Urea. Angew. Chem. Int. Ed. Engl., vol. 30, No. 10, pp. 1314–1315, 1991.*

*Cyanamidhydratase—Analyse Des Proteins Und Seines Gens*, dissertation of Ursula Hildegard Maier, Ludwig Maximillian University, Munich, Germany, 1989 (in German).

English translation of *Cyanamidhydratase—Analyse Des Proteins Und Seines Gens*, dissertation of Ursula Hildegard Maier, Ludwig Maximillian University, Munich, Germany, 1989.

Maier–Greiner, Ursula H., et al., Proc. Natl. Acad. Sci. USA, vol. 88, pp. 4260–4264, 1991.

Maier–Greiner, Ursula H., et al., Angew. Chem. Int. Ed. Engl., vol. 30, No. 10, pp. 1314–1315, 1991.

* cited by examiner

*Primary Examiner*—Elizabeth F. McElwain
(74) *Attorney, Agent, or Firm*—Randee S. Schwartz (57) ABSTRACT

This invention is concerned with the use of cyanamide hydratase as a selection marker in plant transformation. Cyanamide acts as a herbicide and plants transformed with the gene coding for cyanamide hydratase are able to convert the cyanamide into urea which enables the selection of transformed plants by survival under cyanamide pressure.

19 Claims, 3 Drawing Sheets

FIG. 3 pMOG1005

FIG. 4 pMOG1278

FIG. 5 pMOG1295

FIG. 6 pMOG1253

FIG. 7 pMOG873

FIG. 8 pMOG617

| 35S prom. | almv | GU | nos term. | 35S prom. | HPTII | nos term. |

FIG. 9

SEQUENCE LISTING

```
<160> NUMBER OF SEQ ID NOS: 4

<210> SEQ ID NO 1
<211> LENGTH: 900
<212> TYPE: DNA
<213> ORGANISM: Myrothecium verrucaria
<220> FEATURE:
<221> NAME/KEY: CDS
<222> LOCATION: (47)..(778)

<400> SEQUENCE: 1
gtacgatcct acttcctcgc ttatctgctc taaacgattc aacaag atg tct tct        55
                                                   Met Ser Ser
                                                     1 tca gaa gtc aaa gcc aac gga tgg act gcc gtt cca gtc agc gca aag      103
Ser Glu Val Lys Ala Asn Gly Trp Thr Ala Val Pro Val Ser Ala Lys
      5                  10                  15 gcc att gtt gac tcc ctg gga aag ctt ggt gat gtc tcc tca tat tct      151
Ala Ile Val Asp Ser Leu Gly Lys Leu Gly Asp Val Ser Ser Tyr Ser
 20                  25                  30                  35 gtg gaa gat atc gcg ttc cct gcg gca gac aaa ctt gtt gcc gag gca      199
Val Glu Asp Ile Ala Phe Pro Ala Ala Asp Lys Leu Val Ala Glu Ala
                 40                  45                  50 cag gcc ttt gtg aag gcc cga ttg agt ccc gaa acc tac aat cac tcc      247
Gln Ala Phe Val Lys Ala Arg Leu Ser Pro Glu Thr Tyr Asn His Ser
             55                  60                  65 atg cgc gtt ttc tac tgg gga acc gtc atc gcg aga cgt tta ctt ccc      295
Met Arg Val Phe Tyr Trp Gly Thr Val Ile Ala Arg Arg Leu Leu Pro
         70                  75                  80
```

```
                                    -continued gag caa gct aaa gac ttg tct cca agt aca tgg gca ctg aca tgt ctt      343
Glu Gln Ala Lys Asp Leu Ser Pro Ser Thr Trp Ala Leu Thr Cys Leu
         85                  90                  95 ctg cat gac gtt ggt act gcg gag gca tac ttt aca tct aca cga atg      391
Leu His Asp Val Gly Thr Ala Glu Ala Tyr Phe Thr Ser Thr Arg Met
100                 105                 110                 115 tcc ttc gat att tac ggt ggc att aag gct atg gag gtg ctc aag gtc      439
Ser Phe Asp Ile Tyr Gly Gly Ile Lys Ala Met Glu Val Leu Lys Val
                120                 125                 130 ctt ggg agt agc acc gac cag gct gag gct gtt gcc gag gcc atc att      487
Leu Gly Ser Ser Thr Asp Gln Ala Glu Ala Val Ala Glu Ala Ile Ile
            135                 140                 145 cgt cat gag gat gtg ggg gta gat ggc aac atc aca ttc ctc ggt cag      535
Arg His Glu Asp Val Gly Val Asp Gly Asn Ile Thr Phe Leu Gly Gln
        150                 155                 160 ttg atc cag ctg gct acg ctt tat gac aat gtc ggg gcc tac gat ggg      583
Leu Ile Gln Leu Ala Thr Leu Tyr Asp Asn Val Gly Ala Tyr Asp Gly
    165                 170                 175 att gat gat ttt ggt agc tgg gtt gat gac acc aca cgc aac agt atc      631
Ile Asp Asp Phe Gly Ser Trp Val Asp Asp Thr Thr Arg Asn Ser Ile
180                 185                 190                 195 aac acg gca ttc cca cga cat ggt tgg tgt tct tgg ttt gcc tgc acg      679
Asn Thr Ala Phe Pro Arg His Gly Trp Cys Ser Trp Phe Ala Cys Thr
                200                 205                 210 gtt cgt aag gaa gaa agt aac aag cct tgg tgc cac aca acg cat atc      727
Val Arg Lys Glu Glu Ser Asn Lys Pro Trp Cys His Thr Thr His Ile
            215                 220                 225 cct cag ttc gat aaa cag atg gaa gcg aac act ttg atg aag cct tgg      775
Pro Gln Phe Asp Lys Gln Met Glu Ala Asn Thr Leu Met Lys Pro Trp
        230                 235                 240 gag taactctgag taagcagaga atatttagcc gggtagctat agatgaatct           828
Glu ggacaaattc aggcacattt ggtttcacga tacaggtatt ggaaatagct tgcaggaagg    888
tatcatgtca ac                                                        900

<210> SEQ ID NO 2
<211> LENGTH: 244
<212> TYPE: PRT
<213> ORGANISM: Myrothecium verrucaria

<400> SEQUENCE: 2

Met Ser Ser Glu Val Lys Ala Asn Gly Trp Thr Ala Val Pro Val
 1               5                  10                  15

Ser Ala Lys Ala Ile Val Asp Ser Leu Gly Lys Leu Gly Asp Val Ser
                20                  25                  30

Ser Tyr Ser Val Glu Asp Ile Ala Phe Pro Ala Ala Asp Lys Leu Val
            35                  40                  45

Ala Glu Ala Gln Ala Phe Val Lys Ala Arg Leu Ser Pro Glu Thr Tyr
        50                  55                  60

Asn His Ser Met Arg Val Phe Tyr Trp Gly Thr Val Ile Ala Arg Arg
65                  70                  75                  80

Leu Leu Pro Glu Gln Ala Lys Asp Leu Ser Pro Ser Thr Trp Ala Leu
                85                  90                  95

Thr Cys Leu Leu His Asp Val Gly Thr Ala Glu Ala Tyr Phe Thr Ser
            100                 105                 110

Thr Arg Met Ser Phe Asp Ile Tyr Gly Gly Ile Lys Ala Met Glu Val
        115                 120                 125
```

```
Leu Lys Val Leu Gly Ser Ser Thr Asp Gln Ala Glu Ala Val Ala Glu
    130                 135                 140

Ala Ile Ile Arg His Glu Asp Val Gly Val Asp Gly Asn Ile Thr Phe
145                 150                 155                 160

Leu Gly Gln Leu Ile Gln Leu Ala Thr Leu Tyr Asp Asn Val Gly Ala
                165                 170                 175

Tyr Asp Gly Ile Asp Asp Phe Gly Ser Trp Val Asp Asp Thr Thr Arg
            180                 185                 190

Asn Ser Ile Asn Thr Ala Phe Pro Arg His Gly Trp Cys Ser Trp Phe
            195                 200                 205

Ala Cys Thr Val Arg Lys Glu Glu Ser Asn Lys Pro Trp Cys His Thr
    210                 215                 220

Thr His Ile Pro Gln Phe Asp Lys Gln Met Glu Ala Asn Thr Leu Met
225                 230                 235                 240

Lys Pro Trp Glu

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 3
accgagctcg aattcggcac gaggttgaca tgataccttc ctg                    43

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 4
gacctcgaga attcggcacg aggtacgatc ctacttcctc gc                     42
```

SELECTION MARKER

This application is a continuation of pending international application No. PCT/EP98/02979, filed Apr. 17, 1998.

FIELD OF THE INVENTION

This application is concerned with a novel selectable marker, especially with the use of cyanamide hydratase as a selection marker in transformation experiments, more specifically in plant transformation experiments.

BACKGROUND ART

Cyanamide ($H_2N-C\equiv N$) is a nitrile derivate which, like other nitrile derivates, is used in agriculture for stimulation of growth and for plant protection. Cyanamide in aqueous solution or in the form of its calcium salt is used as a fertilizer by providing ammonia to the soil by its metabolic conversion. It has, however, the additional advantage of acting as a herbicide. To use it as fertilizer it has to be applied before sowing.

Chemically, cyanamide belongs to the class of nitrites. In spite of the relatively rare occurrence in nature of compounds containing the nitrile group, enzymes that hydrate this group have been found in bacteria and plants (e.g. Nagasawa T., et al. (1988) Biochem. Biophys. Res. Commun. 155 1008–1016; Endo T. and Watanabe I. (1989) FEBS Lett. 243 61–64). Also in the fungus *Myrothecium verrucaria* a nitrile hydrating enzyme was found (Stransky H. and Amberger A. (1973) Z. Pflanzenphysiol. 70 74–87), which hydrates the nitrile group of cyanamide with formation of urea:

Maier-Greiner et al. have isolated the enzyme and cloned the gene coding for it (Proc. Natl. Acad. Sci. USA 88, 4260–4264, 1991). They have demonstrated that this enzyme shows an extremely narrow substrate specificity, where compounds chemically related to cyanamide are not recognized as substrates.

Selectable markers have to confer a dominant phenotype on transformed cells which is able of being used as a selection criteria. These fall into two classes: one class of genes which confers either cell viability or lethality in the presence of a selective agent and a class of genes which has negligible effects on cell survival but which confers transformed cells with some distinguishing physical characteristic.

In plant transformation the fraction of cells incorporating the novel DNA is generally low, so most stable transformation schemes use markers which ensure the survival of transformed cells in the presence of a selective agent.

A number of selection markers of this first group has been known and used for plant transformation experiments for several years. Included are the enzyme neomycin phosphotransferase (npt) which confers resistance to a group of antibiotics including kanamycin, paromomycin, geneticin and neomycin, mutant forms of the enzyme acetolactate synthase (als) which confer resistance to imidazolinones, sulfonylureas, triazolopyrimidines and pyrimidyloxybenzoates and the enzyme hygromycin 3'-O-phosphotransferase (hpt) which confers resistance to hygromycin. Also available are chloramphenicol transferase (cat) which detoxifies chloramphenicol and dihydrofolate reductase (dhfr) which neutralizes the toxic effects of methotrexate. Another possibility is to use the bar gene for resistance to the herbicide bialaphos (WO 97/05829).

Although there already are a number of selectable markers available, there is still need for another marker. This is due to several reasons:

when transgenic plants are being transformed for a second time with a new construct it is necessary to select for the newly formed transformants with the help of a second selectable marker.

the above mentioned selection markers are not applicable on in all plant species.

some of the compounds which have to be added to enable selection are antibiotics. Spreading of genes which give resistance to antibiotics or herbicides should be minimized as much as possible to avoid the risk of conferring resistance to pathogens.

some of the compounds which have to be added to enable selection are relatively expensive. There is a need for cheaper selection agents.

SUMMARY OF THE INVENTION

The invention now provides the use of a gene coding for cyanamide hydratase (CAH) as a new selection marker. Preferably this can be used for the transformation of plants. The gene comprises the nucleotide sequence of SEQIDNO: 1 or muteins thereof having cyanamide hydratase function.

The invention further comprises a method for the selection of transformed plants which comprises constructing a vector carrying a coding sequence for CAH and a gene of interest, transforming the vector to plants or plant parts or plant cells or callus and growing the resulting transformants in a medium which comprises cyanamide.

The invention is also directed to the use of cyanamide for the selection of plants transformed with a gene coding for CAH.

Further part of the invention are expression cassettes comprising a nucleotide sequence coding for cyanamidehydratase and a gene of interest. Also part of the invention are vectors with this expression cassette and hosts, including Agrobacterium, harboring such a vector. Further, plants transformed with such a vector and/or such an Agrobacterium form part of the invention.

DETAILED DESCRIPTION OF THE INVENTION

The invention is directed to the use of a gene coding for cyanamide hydratase as a selectable marker.

The enzyme cyanamide hydratase (CAH) confers resistance to cyanamide which is a compound that has herbicidal activity. It has now been found that this property of the gene can be used in transformation technology to help in discerning transformed plants from non-transformed plants. However, the herbicidal activity alone is not sufficient to make a gene useful as a selectable marker. For that it is also needed that the gene is expressed in those cells which are submitted to selective conditions. This can be either by constitutive expression or expression in specific tissues like callus, seed, embryogenic tissues and meristematic tissues. Furthermore, it is needed that the gene converts susceptibility of a plant to a toxic compound into tolerance without any residual toxic activity. Also the presence of a large enough 'window' between the concentration of toxic compound needed for selection and the concentration which in the presence of the selection gene at which still growth can be seen is of importance for the use of a selection marker gene. In addition, the system should preferably function sufficiently cell autonomously, such that in a chimaeric tissue (i.e. a tissue with a mosaic of transformed and untransformed cells) untransformed cells are not protected by neighboring transformed cells and therefore survive selection. Surprisingly, the combination of the gene coding for CAH and the toxic properties of cyanamide qualify for their use as selection marker system.

This invention shows that it is possible to select transformants on basis of their tolerance to cyanamide.

An additional advantage is that the cyanamide is converted into urea which is converted in various plants in $NH_3$ and $CO_2$. The $NH_3$ can be used by the plant as source of nitrogen. This is an additional selection possibility to increase the "window" between tolerance and selection. Normally, the culture media contain ammonia and nitrate (contained in the Murashige and Skoog media, see Table 2 and 4). If these are left out or their concentration is decreased the transformed plants containing the CAH gene will convert the cyanamide present in the medium as selection agent into urea and further into ammonia which can be used as nitrogen source. The non-transformed plants are unable to do so, thus in addition to the herbicidal effect of cyanamide they will also suffer from a competitive disadvantage in the area of nitrogen uptake.

The nucleotide sequence coding for CAH is preferably the sequence as depicted in SEQIDNO:1. Also muteins of this sequence may be considered as being part of the invention. Muteins are nucleotide sequences which alter in their nucleotide sequence but still have similar functional and immunological characteristics as the sequence presented in SEQIDNO:1. These muteins are also called functional variants. In addition, the polynucleotides of the invention specifically include those sequences substantially identical (determined as described below) with the gene sequences of the invention and that encode proteins that retain the functional activity of the proteins of the invention. Thus, in the case of the CAH gene disclosed here, the above term includes variant polynucleotide sequences which have substantial identity with the sequences disclosed here and which encode proteins which still have cyanamide degrading activity. "Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of match positions, dividing the number of match positions by the total number of positions in the window of comparison and multiplying the result by 100 to yield the percentage of sequence identity. Optimal alignment of sequences for comparison may be conducted by computerized implementations of known algorithms (e.g., GAP, BESTFIT, FASTA and TFAST in the Wisconsin Genetics Software Package, Genetics Computer Group (GCG), 575 Science Dr., Madison, Wis., or BlastN and BlastX available from the National Center for Biotechnology Information), or by inspection. The term "substantial identity" or "substantial similarity" means that a polypeptide comprises a sequence that is able to hybridize with the target polypeptide under stringent conditions. With stringent conditions a solution of 2*SSC and a temperature of 65° C. is meant.

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine and isoleucine: a group of amino acids having aliphatic-hydroxyl side chains is serine and threonine: a group of amino acids having amide-containing side chains is asparagine and glutamine: a group of amino acids having aromatic side chains is phenylalanine, tyrosine, and tryptophan: a group of amino acids having basic side chains is lysine, arginine and histidine: and a group of amino acids having sulfur-containing side chains is cysteine and methionine.

Substantial identity of polynucleotide sequences means that a polynucleotide comprises a sequence that has at least 70% sequence identity, preferably at least 80%, more preferably at least 90% and most preferably at least 95%. Another indication that nucleotide sequences are substantially identical is if two molecules specifically hybridize to each other under stringent conditions. Stringent conditions are sequence dependent and will be different in different circumstances. Generally, stringent conditions are selected to be about 10° C. lower than the thermal melting point (Tm) for the specific sequence at a defined ionic strength and pH. The Tm is the temperature (under defined ionic strength and pH) at which 50% of the target sequence hybridizes to a perfectly matched probe. The Tm of a hybrid, which is a function of both the length and the base composition of the probe, can be calculated using information in Sambrook, T. et al., (1989) Molecular Cloning—A Laboratory Manual (second edition), Volume 1–3, Cold Spring Harbor Laboratory, Cold Spring. Typically, stringent conditions for a Southern blot protocol involve washing at 65° C. with 0.2×SSC. For preferred oligonucleotide probes, washing conditions are typically about 42° C. in 6×SSC.

The present invention provides a chimeric DNA sequence which comprises an open reading frame capable of encoding a protein having cyanamide hydratase activity. The term chimeric DNA sequence shall mean to comprise any DNA sequence which comprises DNA sequences not naturally found in nature. For instance, chimeric DNA shall mean to comprise DNA comprising the said open reading frame in a non-natural location of the plant genome, even if said plant genome would normally contain a copy of the said open reading frame in its natural chromosomal location. Similarly, the said open reading frame may be incorporated in the plant genome wherein it is not naturally found, or in a replicon or vector where it is not naturally found, such as a bacterial plasmid or a viral vector. Chimeric DNA shall not be limited to DNA molecules which are replicable in a host, but shall also mean to comprise DNA capable of being ligated into a replicon, for instance by virtue of specific adaptor sequences, physically linked to the open reading frame according to the invention. The open reading frame may or may not be linked to its natural upstream and downstream regulatory elements.

The open reading frame may be derived from a genomic library. In this latter it may contain one or more introns separating the exons making up the open reading frame that encodes a protein according to the invention. The open reading frame may also be encoded by one uninterrupted exon, or by a cDNA to the mRNA encoding a protein according to the invention. Open reading frames according to the invention also comprise those in which one or more introns have been artificially removed or added. Each of these variants is embraced by the present invention.

Preferably the open reading frame is derived from the soil fungus *Myrothecium verrucaria* (as described in Maier-Greiner, U.H. et al., Proc. Natl, Acad. Sci. USA 88, 4260–4264, 1991).

In order to be capable of being expressed in a host cell in a way that the expressed protein can confer resistance to the toxic selection agent, a chimeric DNA according to the invention will usually be provided in an expression cassette with regulatory elements enabling it to be recognized by the biochemical machinery of the host and allowing for the open reading frame to be transcribed and translated in the host. It will usually comprise a transcriptional initiation region which may be suitably derived from any gene capable of being expressed in the host cell of choice, as well as a translational initiation region for ribosome recognition and attachment. In eukaryotic plant cells, an expression cassette usually comprises in addition a transcriptional termination region located downstream of said open reading frame, allowing transcription to terminate and polyadenylation of the primary transcript to occur. In addition, the codon usage may be adapted to accepted codon usage of the host of choice. The principles governing the expression of a chimeric DNA construct in a chosen host cell are commonly understood by those of ordinary skill in the art and the construction of expressible chimeric DNA constructs is now routine for any sort of host cell, be it prokaryotic or eukaryotic.

In order for the open reading frame to be maintained in a host cell it will usually be provided in the form of a replicon comprising said open reading frame according to the invention linked to DNA which is recognized and replicated by the chosen host cell. Accordingly the selection of the replicon is determined largely by the host cell of choice. Such principles as govern the selection of suitable replicons for a particular chosen host are well within the realm of the ordinary skilled person in the art.

A special type of replicon is one capable of transferring itself, or a part thereof, to another host cell, such as a plant cell, thereby co-transferring the open reading frame according to the invention to said plant cell. Replicons with such capability are herein referred to as vectors. An example of such vector is a Ti-plasmid vector which, when present in a suitable host, such as *Agrobacterium tumefaciens,* is capable of transferring part of itself, the so-called T-region, to a plant cell. Different types of Ti-plasmid vectors (vide: EP 0 116 718 B1) are now routinely being used to transfer chimeric DNA sequences into plant cells, or protoplasts, from which new plants may be generated which stably incorporate said chimeric DNA in their genomes. A particularly preferred form of Ti-plasmid vectors are the so-called binary vectors as claimed in (EP 0 120 516 B1 and U.S. Pat. No. 4,940,838). Other suitable vectors, which may be used to introduce DNA according to the invention into a plant host, may be selected from the viral vectors, e.g. non-integrative plant viral vectors, such as derivable from the double stranded plant viruses (e.g. CaMV) and single stranded viruses, gemini viruses and the like. The use of such vectors may be advantageous, particularly when it is difficult to stably transform the plant host. Such may be the case with woody species, especially trees and vines.

The expression "host cells incorporating a chimeric DNA sequence according to the invention in their genome" shall mean to comprise cells, as well as multicellular organisms comprising such cells, or essentially consisting of such cells, which stably incorporate said chimeric DNA into their genome thereby maintaining the chimeric DNA, and preferably transmitting a copy of such chimeric DNA to progeny cells, be it through mitosis or meiosis. Such host cells can be prokaryotic organisms such as bacteria, but also eukaryotic organisms such as yeast. Also cells from eukaryotes in tissue culture, such as cell cultures of plants or animals like mammals can be envisaged to stably incorporate the chimeric DNA. According to a preferred embodiment of the invention plants are provided, which essentially consist of cells which incorporate one or more copies of said chimeric DNA into their genome, and which are capable of transmitting a copy or copies to their progeny, preferably in a Mendelian fashion. By virtue of the transcription and translation of the chimeric DNA according to the invention those cells that produce the CAH will show enhanced resistance to cyanamide. Although the principles which govern transcription of DNA in plant cells are not always understood, the creation of chimeric DNA capable of being expressed in tissue which is subject to selection by cyanamide, such as callus, seed, embryogenetic tissues or meristematic tissues, or constitutive expression, is now routine. Transcription initiation regions routinely in use for expression of the transformed polynucleotide in a constitutive way are promoters obtainable from the cauliflower mosaic virus, notably the 35S RNA and 19S RNA transcript promoters and the so-called T-DNA promoters of *Agrobacterium tumefaciens.* In particular to be mentioned are the nopaline synthase promoter, octopine synthase promoter (as disclosed in EP 0 122 791 B1) and the mannopine synthase promoter. In addition plant promoters may be used, which may be substantially constitutive, such as the rice actin gene promoter. The choice of the promoter is not essential, although it must be clear that constitutive high-level promoters should show expression in tissue on which the selection takes place. It is further known that duplication of certain elements, so-called enhancers, may considerably enhance the expression level of the DNA under its regime (vide for instance: Kay R. et al. (1987), Science 236, 1299–1302: the duplication of the sequence between −343 and −90 of the CaMV 35S promoter increases the activity of that promoter). In addition to the 35S promoter, singly or doubly enhanced, examples of high-level promoters are the light-inducible ribulose bisphosphate carboxylase small subunit (rbcSSU) promoter and the chlorophyll a/b binding protein (Cab) promoter. Also envisaged by the present invention are hybrid promoters, which comprise elements of different promoter regions physically linked. A well known example thereof is the so-called CaMV enhanced mannopine synthase promoter (U.S. Pat. No. 5,106,739), which comprises elements of the mannopine synthase promoter linked to the CaMV enhancer.

Specifically with monocot transformation the use of introns between promoter and selectable marker gene enhances expression. The term "promoter" thus refers to a region of DNA upstream from the structural gene and involved in recognition and binding RNA polymerase and other proteins to initiate transcription. A "plant promoter" is a promoter capable of initiating transcription in plant cells. A "constitutive promoter" is a promoter which is active under most environmental conditions and states of development or cell differentiation.

A constitutive promoter is preferable for this invention because selection for transformants may be made at various stages and with various tissues. Thus a constitutive promoter does not limit the selection possibilities.

Choice of an appropriate constitutive promoter in this respect is of importance for the use of other promoters in the same transformation process. It is known that duplication of promoters is influential to the expression of the genes under control of said promoters. Since it is the goal of the expression of a selection marker only to be used for selection of plants which are simultaneously transformed with a gene of interest one should keep in mind that using the same promoter for the selectable marker gene and the gene of interest can cause problems.

As regards the necessity of a transcriptional terminator region, it is generally believed that such a region enhances the reliability as well as the efficiency of transcription in plant cells. Use thereof is therefore strongly preferred in the context of the present invention.

As regards the applicability of the invention in different plant species, it has to be mentioned that one particular embodiment of the invention is merely illustrated with transgenic tomato, potato, rice and Arabidopsis plants as an example, the actual applicability being in fact not limited to these plant species.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

"Transformation of plants" is meant to be any method in which DNA is introduced into a plant. Such a transformation process should not necessarily contain a regeneration and/or tissue culture period.

Transformation of plant species is now routine for an impressive number of plant species, including both the Dicotyledoneae as well as the Monocotyledoneae. In principle any transformation method may be used to introduce chimeric DNA according to the invention into a suitable ancestor cell. Methods may suitably be selected from the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-intergrative) viruses, in planta *Agrobacterium tumefaciens* mediated gene transfer by infiltration of plants or transformation of mature pollen or microspores (EP 0 301 316) and the like. A preferred method according to the invention comprises Agrobacterium-mediated DNA transfer. Especially preferred is the use of the so-called binary vector technology as disclosed in EP A 120 516 and U.S. Pat. No. 4,940,838).

Tomato transformation is preferably done essentially as described by Van Roekel et al. (Van Roekel, J. S. C., et al. Plant Cell Rep. 12, 644–647). Potato transformation is preferably done essentially as described by Hoekema et al. (Hoekema, A., et al. 7, 273–278 1989).

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or (tissue) electroporation (Shimamoto, et al., Nature 338, 274–276, 1989). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, Plant Cell, 2, 603–618, 1990). Wheat plants have been regenerated from embryogenic suspension culture by selecting embryogenic callus for the establishment of the embryogenic suspension cultures (Vasil Bio/Technol. 8, 429–434, 1990). The combination with transformation systems for these crops enables the application of the present invention to monocots.

Monocotyledonous plants, including commercially important crops such as rice and corn are also amenable to DNA transfer by Agrobacterium strains (vide WO 94/00977; EP 0 159 418 B1; Gould J., Michael D, Hasegawa O, Ulian E C, Peterson G, Smith R H, Plant. Physiol. 95, 426–434, 1991).

To obtain transgenic plants capable of expressing more than one chimeric gene, a number of alternatives are available including the following:

A. The use of DNA, e.g a T-DNA on a binary plasmid, with a number of modified genes physically coupled to a second selectable marker gene. The advantage of this method is that the chimeric genes are physically coupled and therefore migrate as a single Mendelian locus. The invention is especially useful in this respect, since it enables for a second selectable marker which can be introduced next to an already existing selectable marker-gene of interest combination. Thus selection for retransformants can be performed irrespective of the nature of the first selectable marker.

B. Cross-pollination of transgenic plants each already capable of expressing one or more chimeric genes, preferably coupled to a selectable marker gene, with pollen from a transgenic plant which contains one or more chimeric genes coupled to another selectable marker. Afterwards the seed, which is obtained by this crossing, maybe selected on the basis of the presence of the two selectable markers, or on the basis of the presence of the chimeric genes themselves. The plants obtained from the selected seeds can afterwards be used for further crossing. In principle the chimeric genes are not on a single locus and the genes may therefore segregate as independent loci. Also here the option to select for both selectable markers is one of the advantages of the present invention.

C. The use of a number of a plurality of chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.
D. Consecutive transformation of transgenic plants already containing a first, second, (etc), chimeric gene with new chimeric DNA, optionally comprising a selectable marker gene. As in method B, the chimeric genes are in principle not on a single locus and the chimeric genes may therefore segregate as independent loci.
E. Combinations of the above mentioned strategies.

The actual strategy may depend on several considerations as maybe easily determined such as the purpose of the parental lines (direct growing, use in a breeding program, use to produce hybrids) but is not critical with respect to the described invention.

Although not necessary for this invention, it is known that practically all plants can be regenerated from cultured cells or tissues. The means for regeneration vary from species to species of plants, but generally a suspension of transformed protoplasts or a petri plate containing transformed explants is first provided. Shoots may be induced directly, or indirectly (from callus) via organogenesis or embryogenesis and subsequently rooted. Next to the selective compound, the culture media will generally contain various amino acids and hormones, such as auxin and cytokinins. Efficient regeneration will depend on the medium, on the genotype and on the history of the culture. If these three variables are controlled regeneration is usually reproducable and repeatable.

After stable incorporation of the transformed gene sequences into the transgenic plants, the traits conferred by them can be transferred to other plants by sexual crossing. Any of a number of standard breeding techniques can be used, depending upon the species to be crossed.

EXAMPLE 1

Cloning the Fungal Gene Encoding Cyanamide Hydratase (CAH) in a Heterologous Expression Cassette a. Constructs for Transformation to Dicots Construct pMOG874 contains the coding region from the cyanamide hydratase gene from the soil fungus *Myrothecium verrucaria* which is operably linked to the CaMV 35S promoter and the CaMV 35S terminator. This chimeric gene is cloned in the binary vector pBI101 (Jefferson et al. EMBO J. 6, 3901, 1987) replacing the β-glucuronidase coding region and the nopaline synthase terminator.

The construct is obtained by adding an XhoI site at the 5' end and a SstI site at the 3' end of a 899 bp cDNA fragment of CAH (position 235-1197 of sequence published by Maier-Greiner et al. (1991) Proc. Natl. Acad. Sci. USA 88:4260–4264) by PCR using the primers p1:5'ACCGAGCTCGAATTCGGCACGAGGTTGACA TGATACCTTCCTG 3' and p2:5'GACCTCGAGAATTCGGCACGAGGTACGATCC TACTTCCTCGC 3' between the sites XhoI and SstI of the plant expression vector pRT101, both sites belonging to the polylinker which is inserted between the 35S promoter and the 35S termination signal of pRT101 (Töpfer et al. 1987, Nucl. Acids Res. 15: 5890).

The chimeric gene is then cleaved with PstI, overhanging ends are polished with T4 DNA polymerase and the fragment is cloned blunt in the SmaI site of pBIN19 (Bevan, M. Nucl. Acids Res. 12:8711–8721, 1984).

In construct pMOG1156 an additional β-glucuronidase gene operably linked to the 35S promoter and the 35S terminator is inserted as XhoI/SalI fragment in the SalI site of pMOG874.

Both constructs contain in addition to the novel CAH selection marker the conventional NPTII selection marker linked to the nopaline synthase promoter and the nopaline synthase terminator as it is in pBIN19.

b. Constructs for Transformation to Monocots

Figure 8:
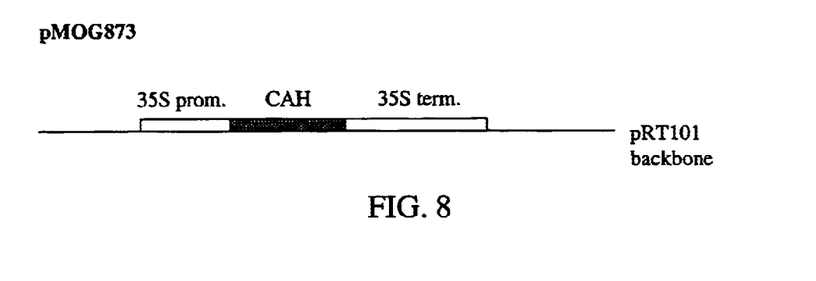

In the same way as pMOG874 was made the expression cassette was cloned into a high copy vector (pRT101, Töpfer, R. et al., Nucl. Acids Res. 15, 5890, 1987) resulting in pMOG873 (FIG. 8)

Figure 1:
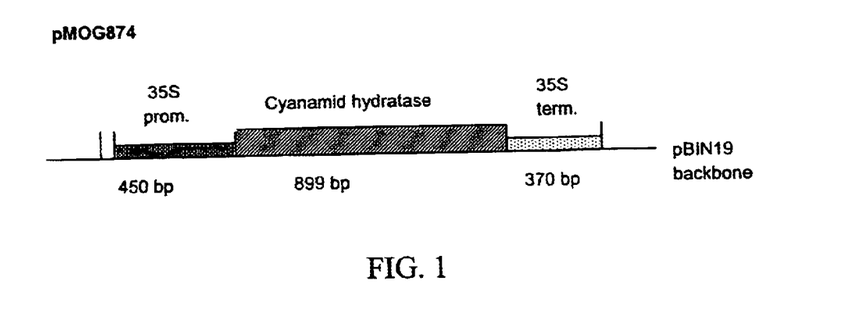
FIG. 1. Outline of the T-DNA in pMOG874
FIG. 2. Outline of the T-DNA in pMOG1156
FIG. 3 Outline of the T-DNA in pMOG22
FIG. 4 Outline of the T-DNA in pMOG1005
FIG. 5 Outline of the T-DNA in pMOG1278
FIG. 6 Outline of the T-DNA in pMOG1295
FIG. 7 Outline of the T-DNA in pMOG1253
FIG. 8 Outline of the expression cassette in pMOG873
FIG. 9 Outline of the expression cassette in pMOG617
Figure 2:
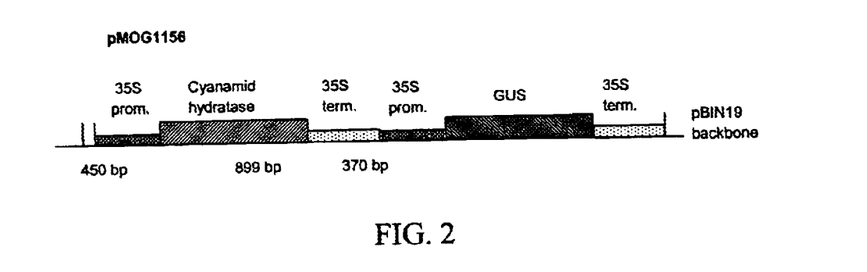
Figure 3:
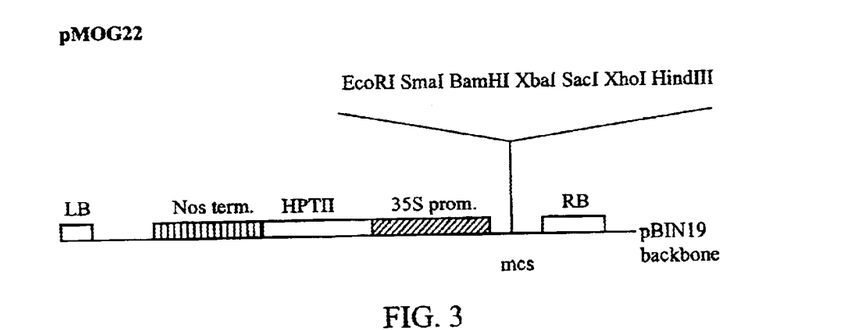
Figure 4:
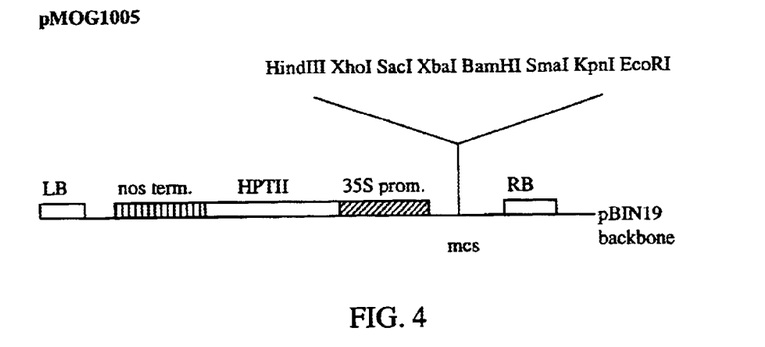
Figure 5:
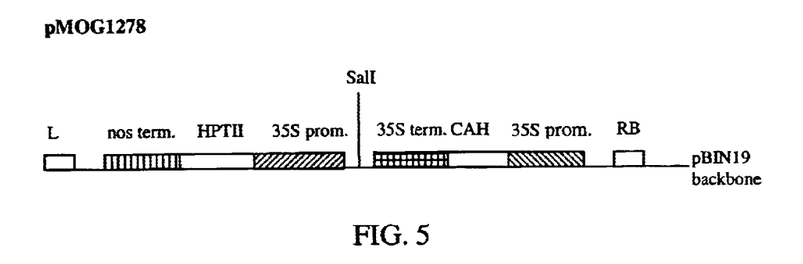
Figure 6:
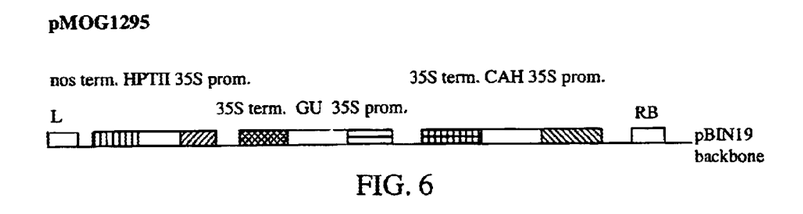
Figure 7:
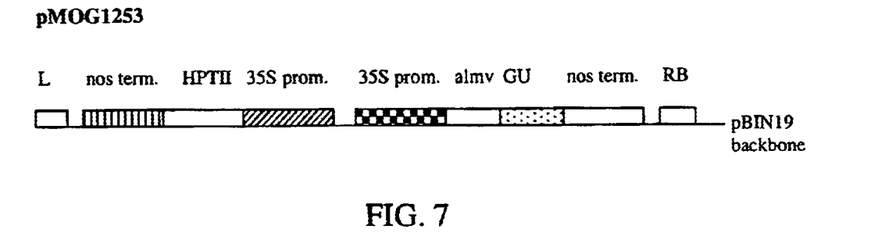
Figure 9:
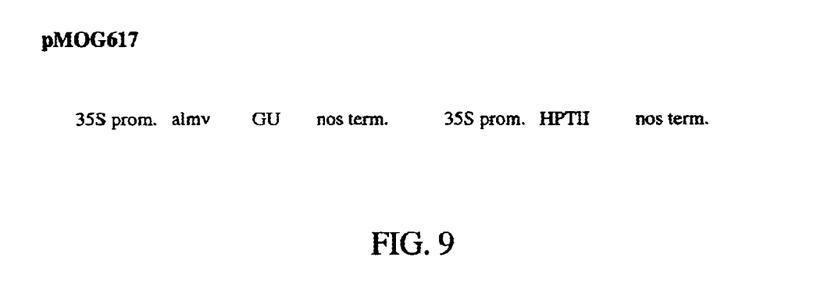

A derivative of pMOG22 (FIG. 3, deposited at the Centraal Bureau voor Schimmelcultures, Baarn, The Netherlands on Jan. 29, 1990, under no. CBS 101.90) was made by introducing a Kpn I restriction site in the polylinker of pMOG22 between the EcoR I and Sma I site. The orientation of the polylinker was also reversed. This plasmid, denominated pMOG1005, contains a hygromycin resistance gene between the left and right T-DNA borders (FIG. 4). The 1.7 kb expression cassette comprising the cah gene under control of the 35S promoter and the 35S terminator was cloned between the Hind III and BamH I restriction sites. This plasmid was denominated pMOG1278 (FIG. 5). Binary vector pMOG1295 (FIG. 6) is a derivative of pMOG1278 and contains in the Sal I restriction site a GUS-expression cassette as described in Vancanneyt, G. et al. (Mol. Gen. Genet., 220, 245–250, 1990). pMOG1253 was made departing from pMOG18 (Sijmons, P. C. et al., Bio/Technol. 8, 217–221, 1990) which contains the double enhanced 35S promoter, the ALMV RNA4 leader sequence, the GUS-gene and the nos-terminator in an expression cassette as an EcoR I-Hind III fragment. The plasmid p35S GUS INT (Vancanneyt, 1990) was digested with SnaB I and Msc I; the resulting 426 bp fragment, containing part of the coding region for the GUS gene and ST-LS1 intron, was isolated and cloned into pMOG18 linearized with SnaB I and Msc I. From the resulting plasmid a 3189 bp EcoR I-Hind III fragment was isolated and cloned into pMOG22, resulting in pMOG1253 (FIG. 7). pMOG617 (FIG. 9) was made by cloning the hygromycin expression cassette from pMOG22 in the Hind III site of high copy vector pMOG18.

EXAMPLE 2

Potato Transformation

Described below is the method used for transformation of stem segments of Solanum tuberosum cv. Kardal using *Agrobacterium tumefaciens*. Nodal explants from in vitro grown potato plants were used 3 to 8 weeks after transfer. The plants were grown on Multiplication Medium (MUM) under a 16 h light period (1700 lux) at 24° C. and a 8 h dark period at 21° C. (The various media can be found in Table 2). Stem segments of approximately 5 mm were cut on sterile filter paper soaked with Washing Medium (WAM) and collected in a flask containing Washing Medium. For approximately 300 explants the Washing Medium was replaced by Pre cultivation Medium (PRM). The flasks were cultured at 80 rpm at the same culture conditions as described above for approximately 24 h. All binary vectors used in this study contained the nptII gene as a plant selectable marker and the nptIII as bacterial selectable marker. Plasmid pMOG410 additionally harbored a chimeric gus gene containing an intron (Vancanneyt et al. Mol. Gen. Genet., 220, 245–250, 1990). Plasmid pMOG1156 additionally harbored the gus gene and the chimeric cah gene encoding cyanamide hydratase. Plasmid pMOG874 additionally harbored the cah gene. Plasmids were maintained in *E.coli* and *A. tumefaciens* under kanamycin selection.

The Agrobacterium strain used in this study harbored a rifampicin selection marker in a C58 chromosomal background. The construction of the helper strain EHA105 is described by Hood et al. (1993), Transg. Res. 2, 208–218.

Agrobacteria were grown overnight in LB medium with antibiotics (rifampicin 20 mg/l, kanamycin 100 mg/l). The overnight culture was diluted to $OD_{600}=0.1$ and grown to $OD_{600}=0.3$ in LB without antibiotics in approximately 2 h time. Bacterial suspensions were centrifuged at 1600×g for 15 minutes at room temperature. Bacteria were resuspended in Washing Medium and used for cocultivation experiments. The Pre cultivation Medium was removed from the flasks and replaced by the Agrobacterium suspension. The flasks were incubated for 20 minutes after which the explants were rinsed twice with Washing Medium. The explants were dried on sterile filter paper and incubated for 48 h on plates containing Cocultivation Medium (COM). Then, the explants were transferred to Post cultivation Medium (POM) and incubated for 72 h. The explants were then transferred to Shoot inducing Medium (SIM) containing several concentrations cyanamide or kanamycin. After two weeks the explants were subcultured on the same medium and approximately three weeks later the explants were placed on Shoot elongation Medium (SEM) containing cyanamide or kanamycin as mentioned above. When shoots were large enough to cut they were transferred to Root inducing Medium (RIM). Shoots that were able to root were then transferred to Root inducing Medium containing 50 mg/l cyanamide or 30 mg/l kanamycin. Simultaneously the transgenic nature of the shoots was determined by testing leaflets of the rooted shoots for expression of the gus gene using a histochemical GUS assay. It appeared that for pMOG1156 rooting of transgenic shoots on medium containing cyanamide was completely correlated with expression of the gus gene.

TABLE 1

Transformation frequencies of potato stem segments

| Selection during regeneration (mg/l) | Nr. of inoculated explants | No. of excised shoots | No. of rooting shoots | No. of gus + shoots |
|---|---|---|---|---|
| pMOG1156 (cah-gus-nptII) | | | | |
| Cyanamide 40 | 48 | 15 | 2 | 2 |
| Cyanamide 30 | 48 | 50 | 12 | 12 |
| Cyanamide 20 | 48 | 56 | 6 | 6 |
| Kanamycin 50 | 48 | 26 | 16 | 16 |
| pMOG410 (gus-nptII) | | | | |
| Cyanamide 40 | 62 | 0 | 0 | 0 |
| Cyanamide 30 | 62 | 10 | 0 | 0 |
| Cyanamide 20 | 62 | 48 | 0 | 0 |
| Kanamycin 50 | 58 | 24 | 13 | 12 |
| pMOG874 (cah-nptII) | | | | |
| Cyanamide 40 | 58 | 10 | 1 | n.d. |
| Cyanamide 30 | 58 | 40 | 8 | n.d. |
| Cyanamide 20 | 58 | 81 | 2 | n.d. |
| Kanamycin 50 | 58 | 34 | 26 | n.d. | n.d.: not determined.

TABLE 2

Composition of the various media.

| Medium: | WAM | PRM | COM | POM | SIM | SEM | RIM | MUM |
|---|---|---|---|---|---|---|---|---|
| Macro salts | 1 × MS | 1 × MS | 1 × MS | 1 × MS | 1 × MS | 1 × MS | 1/2 × MS | 1/2 × MS |
| Vitamins | B5 | B5 | B5 | B5 | B5 | B5 | 1/2R3 | 1/2R3 |
| Sucrose | 3% | 3% | 3% | 3% | 3% | 3% | 1% | 1% |
| Agar | — | 0.8% | 0.8% | 0.8% | 0.8% | 0.8% | 0.8% | 0.8% |
| MES (gr/l) | 0.5 | 0.5 | 0.5 | 0.5 | 0.5 | 0.5 | 0.5 | 0.5 |
| pH | 5.8 | 5.8 | 5.8 | 5.8 | 5.8 | 5.8 | 5.8 | 5.8 |
| Zeatin Riboside (mg/l) | — | 0.5 | 0.5 | 3.0 | 3.0 | 0.3 | — | — |
| 2,4-D | — | 1.0 | 1.0 | — | — | — | — | — |
| IBA | — | — | — | — | — | — | 0.1 | — |
| Cefotaxim | — | — | — | 200 | 200 | 200 | 100 | — |
| Vancomycin | — | — | — | 100 | 100 | 100 | 50 | — |

MS: Murashige and Skoog, Physiol. 15, 473–479, 1962
B5: Gamborg B5 (Gamborg, Orl et al., Exp. Cell Res. 50, 151–158, 1986)

EXAMPLE 3

Tomato Transformation

Described below is the method used for transformation of cotyledons of *Lycopersicon esculentum* cv. Money Maker using *Agrobacterium tumefaciens*. The binary vectors and Agrobacteria strains for this transformation method are identical to those described above. Tomato seedlings were germinated on Germination Medium (GEM) under a 16 h light period (1700 lux) at 24° C. and a 8 h dark period at 21°

C. (The contents of the various media can be found in Table 4). Cotyledon explants of 5 to 7 day old seedlings were cut on sterile filter paper soaked with Washing Medium (WAM) and placed on plates containing Cocultivation Medium (COM). The plates, each containing approximately 50 explants, were incubated overnight under the same conditions as described above.

The pre incubated explants were carefully submerged in the Agrobacterium inoculum for 20 minutes.

The explants were then blotted dry on sterile filter paper and incubated for 48 h on the second set of Cocultivation plates. In procession the explants were incubated for 72 h on plates containing Postcultivation Medium (POM) after which the explants were transferred to Shoot inducing Medium (SIM) containing several concentrations of cyanamide or kanamycin. Every three weeks the explants were subcultured on the same medium. After approximately 8–12 weeks shoots were excised and placed on Root inducing Medium (RIM). Shoots that were able to root were then transferred to Root inducing Medium containing 50 mg/l cyanamide or 30 mg/l kanamycin. Simultaneously leaflets of the rooted shoots were tested for expression of the gus gene in a histochemical GUS assay.

TABLE 3

Transformation results of tomato cotyledon explants

| Selection during regeneration (mg/l) | Nr. of inoculated explants | No. of excised shoots | No. of rooting shoots | No. of gus + shoots |
|---|---|---|---|---|
| pMOG1156 (gus-nptII-cah) | | | | |
| Cyanamide 40 | 30 | 5 | 3 | 3 |
| Cyanamide 30 | 30 | 5 | 0 | 0 |
| Cyanamide 20 | 30 | 0 | 0 | 0 |
| Kanamycin 100 | 30 | 5 | 3 | 4 |
| pMOG410 (gus-nptII) | | | | |
| Cyanamide 40 | 30 | 0 | 0 | 0 |
| Cyanamide 30 | 30 | 3 | 0 | 0 |
| Cyanamide 20 | 30 | 0 | 0 | 0 |
| Kanamycin 100 | 30 | 4 | 3 | 3 |
| pMOG874 (cah-nptII) | | | | |
| Cyanamide 40 | 35 | 1 | 1 | n.d. |
| Cyanamide 30 | 35 | 0 | 0 | n.d. |
| Cyanamide 20 | 35 | 2 | 0 | n.d. |
| Kanamycin 100 | 35 | 4 | 1 | n.d. | n.d.: not determined

TABLE 4

Composition of the various media

| Medium: | WAM | COM | POM | SIM | RIM | GEM |
|---|---|---|---|---|---|---|
| MS Macro salts | 1x | 1x | 1x | 1x | 1x | 1/2x |
| Vitamins | B5 | B5 | B5 | B5 | B5 | B5 |
| Sucrose | 3% | 3% | 3% | — | 1% | 1% |
| Glucose | — | — | — | 1% | — | — |
| Agar | — | 0.8% | 0.8% | 0.8% | 0.8% | 0.8% |
| MES (gr/l) | 0.5 | 0.5 | 0.5 | 0.5 | 0.5 | 0.5 |
| pH | 5.8 | 5.8 | 5.8 | 5.8 | 5.8 | 5.8 |
| Zeatin Riboside (mg/l) | — | 2.0 | 2.0 | 2.0 | — | — |
| IAA | — | 0.1 | 0.1 | 0.1 | — | — |
| 2,4-D | — | 0.05 | — | — | — | — |
| IBA | — | — | — | — | 0.25 | — |
| Carbenicillin | — | — | — | 500 | — | — |
| Cefotaxim | — | — | 200 | — | 200 | — |

TABLE 4-continued

Composition of the various media

| Medium: | WAM | COM | POM | SIM | RIM | GEM |
|---|---|---|---|---|---|---|
| Vancomycin | — | — | 50 | — | — | — |
| Acetosyringone (mM) | — | 0.2 | — | — | — | — |

EXAMPLE 4

Arabidopsis Transformation

Described below is the method used for transformation of root segments of *Arabidopsis thaliana* cv. C24 using *Agrobacterium tumefaciens*. The binary vectors for this transformation method are identical to those described above.

Six mg of Arabidopsis seeds were germinated in a flask containing liquid Germination Medium (GM) under 16 h light period (1700 lux) at 24° C. and a 8 h dark period at 21° C. at 80 rpm. (The contents of various media can be found in Table 4). Roots of 9 days old seedlings were isolated in a sterile petridish and collected in a drop of Germination Medium (GM). Roots were cut in segments of approximately 3–5 mm and approximately 100 explants were spread evenly on a nylon membrane (O 8 cm) which was placed on plates containing Callus Inducing Medium (CIM). The plates were incubated 3 days under the same conditions as described above.

The Agrobacterium strain used in this study harbored a rifampicin selection marker in a C 58 chromosomal background. The construction of the helper strain MOG101 is described by Hood et al. (1993).

Agrobacteria were grown overnight in LB medium with antibiotics (rifampicin 20 mg/l, kanamycin 100 mg/l). The overnight culture was diluted 1:10 in LB without antibiotics and grown for approximately 3 hours. Bacterial suspensions were centrifuged at 1600×g for 15 minutes at room temperature. Bacteria were resuspended in GM and adjusted to OD600=0.1 and used for cocultivation.

The membrane containing approximately 100 explants was incubated for 2 minutes with the Agrobacterium suspension and dried on sterile filter paper to remove excess of bacteria. The membrane with explants are cultured for 48 h on CIM plates. After rinsing the membrane and explants with liquid GM these were incubated on Shoot Induction Medium (SIM) plates containing several concentrations of cyanamide or kanamycin. After 5 days the membrane with the explants was transferred to the same medium (SIM) for subculture. The second subculture was after 2 weeks. Approximately four weeks after cocultivation 60 shoots per cyanamide concentration were excised and placed on plates with Shoot Elongation Medium (SEM) containing 30 mg/l cyanamide. Shoots which were able to root are tested on their transgenic character by testing leaflets and flowers for expression of the gus gene using a histochemical GUS assay.

Three experiments were performed. Shoots obtained from Exp. 98-8 and 98-11 were transferred to rooting medium (SEM) containing 30 mg/litre cyanamide. Shoots obtained from Exp. 98-13 were transferred to rooting medium containing the same concentration as the selection medium (SIM), for results see Table 4a. The shoots obtained from the kanamycin selection (50 mg/litre) were transferred to rooting medium containing 25 mg/litre Kanamycin.

TABLE 4

Media required for *Arabidopsis thaliana* C24 root transformation

| Media components | Media | GM | CIM | SIM | SEM |
|---|---|---|---|---|---|
| Ingredients | macro elements | B5 | B5 | B5 | MS |
| | micro elements | B5 | B5 | B5 | MS |
| | vitamins | B5 | B5 | B5 | B5 |
| | sucrose (g/l) | | | | 10 |
| | glucose (g/l) | 20 | 20 | 20 | |
| | Daichin agar (g/l) | | 10 | 10 | 10 |
| Hormones | 2,4-D | | 0.5 | | |
| | kinetin | | 0.05 | | |
| | 2-ip | | | 5 | |
| | IAA | | | 0.15 | |
| Antibiotics | vancomycin | | | 100 | 50 |
| | carbenicillin | | | 500 | |
| | cefotaxime | | | | 100 |

Root explants transformed with pMOG 410 were not able to regenerate on cyanamide containing medium. Even 20 mg/litre cyanamide was already enough to prevent regeneration of explants transformed with a construct without the cah gene. At 20 till 40 mg/litre cyanamide some callus development was observed, but at 50 mg/litre and higher explants were not viable and turned completely brown.

On the other hand explants transformed with the cah gene (PMOG 1156) were able to regenerate at all cyanamide concentrations, even at 80 mg/litre. At lower concentrations the regeneration of shoots was faster than with kanamycin.

Although more shoots were available 60–65 shoots were harvested per treatment and placed on rooting medium. At the lower cyanamide concentrations the same amount of shoots developed as with kanamycin selection (approx. 70–100 per petridish).

There is a clear correlation between callus development and GUS expression on cyanamide selection with root explants transformed with pMOG 1156 (FIG. 4b). GUS analysis of shoots obtained on cyanamide 0 mg/litre (NS) showed no staining, indicating that cyanamide is needed to obtain transgenic shoots.

TABLE 4a

Results Arabidopsis transformation with pMOG 1156

| Conc. of Cyanamide (mg/litre) | Experiment 98-8 | | Experiment 98-11 | | Experiment 98-13 | |
|---|---|---|---|---|---|---|
| | Nr. of plants[1] | % Shoots[2] rooting | Nr. of plants | % Shoots rooting | Nr. of plants | % Shoots rooting |
| C20 | 0 | 0 | 1 | 1.7 | 3 | 4.8 |
| C30 | 4 | 6.3 | 2 | 3.2 | 9 | 14.5 |
| C40 | 5 | 8.2 | 3 | 4.5 | 1 | 1.6 |
| C50 | nd. | nd. | 5 | 8.1 | 0 | 0 |
| C60 | 5 | 8.2 | nd. | nd. | 4 | 6.0 |
| C80 | 9 | 13.8 | 10 | 15.6 | 8 | 11.4 |
| K50 | 29 | 46.8 | 19 | 47.5 | 14 | 20.6 |

[1]The total number of plants consists of those shoots developed into plants and able to root on cyanamide containing medium.
[2]% Shoots rooting = Nr. of plants/Total nr. of shoots * 100%
[3]% of blue stained plants compared to nr. of plants TABLE 4b Percentaqe of GUS expressing Arabidopsis plants obtained via cyanamide or kanamycin selection.

| | pMOG 410 | pMOG 1156 | |
|---|---|---|---|
| Treatment | $C^3 30^5$ | $C30^5$ | Same conc. as treatment[5] |
| C20 | nd | $0^1$ | 0 |
| C30 | nd | 75–100 | 78 |
| C40 | nd | 40–100 | 100 |
| C50 | nd | 80 | nd. |
| C60 | nd | 80 | 100 |
| C80 | nd | 67–90 | 100 |
| $K^4 50$ | $100^2$ | 82–92 | 100 |

[1]% of plants staining blue
[2]All pMOG 410 shoots are rooted on Kanamycin 25 mg/litre
[3]C = Cyanamide (mg/litre)
[4]K = Kanamycin (mg/litre)
[5]concentration in rooting medium

EXAMPLE 5

Rice Transformation

Described below is the method used for transformation of callus derived from scutellum of mature embryos of *Oryza sativa* cv. Taipei 309 using *Agrobacterium tumefaciens* strain LBA1119-pMOG1295 (harboring the cah-gene) and strain LBA1119-pMOG1253 (control). Sterile dehusked rice seeds were germinated on plates containing Callus Induction Medium (CIM) in the dark at 28° C. (The contents of various media can be found in Table 5). After 3 weeks embryogenic callus derived from the scutellum is isolated and subcultured on the same medium under the same conditions. After 2–3 weeks embryogenic calli were cut in segments of approximately 2–3 mm and cultured plates containing CIM for 4 days. The Agrobacterium strains used in this study harbored a rifampicin selection marker in a C 58 chromosomal background. The construction of the helper strain EHA105 is described by Hood et al. (1993). Agrobacteria were grown for 4 days on plates containing AB medium with antibiotics (rifampicin 20 mg/l, kanamycin 100 mg/l ). Agrobacteria were collected in LIM and the OD600 was adjusted till 1.0–1.5. This suspension was used for cocultivation. Calli were incubated for 10 minutes with the Agrobacterium suspension and dried on sterile filter paper to remove excess of bacteria. Calli were cultured for 48 h on Coculture Medium (COM) plates at 25° C. in the dark. 50 pMOG1295 calli and 20 pMOG1253 calli were cultured per concentration of cyanamid. The following concentrations of cyanamide were used: 0, 15, 30, 60, 100, 150, 200, 300 and 500 mg/l. Hygromycin was applied in a concentration of 50 mg/l. Calli were incubated on First Selection Medium (FSM) plates containing several concentrations of cyanamide or hygromycin at 28° C. in the dark. After 3 weeks the calli were transferred to Embryo Induction Medium I (EIM I) containing the same concentration of cyanamide or hygromycin . After another 3 weeks the calli were subcultured on Embryo Induction Medium II (EIM II) containing the same concentration of cyanamide or an increased concentration of hygromycin (75 mg/l). Calli were transferred to Shoot Induction Medium (SIM) containing the same concentration of cyanamide as during FSM, EIM I, EIM II and were cultured under 12 hours light period (2600 LUX) and 12 hours dark at 28 ° C. Approximately 3 weeks after transferring calli to SIM, shoots were regenerating and excised and placed in jars containing Pre-Greenhouse Medium (PGM). No calli were formed at concentrations of 100 mg/l or higher of cyanamid. At 15 mg/l cyanamide the regeneration frequency of callus from both constructs was the same (pMOG1253 7 out of 16 calli were able to regenerate, pMOG1295 17 out of 44). At 30 mg/l cyanamide only 11 calli of pMOG1295 showed green callus development and 6 were able to be regenerated.

transformed with pMOG617 were found resistant to hygromycin, while for the transformation with pMOG873 7 calli survived cyanamide 20 mg/l in the first experiment (results from the second experiment not yet available) and 0+4 calli remained viable on 40 mg/l cyanamide. No calli were formed at concentrations of 50 mg/l cyanamide or higher. The transgenic nature was confirmed by testing parts

TABLE 5

Media required for Oryza sativa Taipei 309 transformation

| Media components | Media | CIM | COM | LIM | FSM | EIM I | EIM II | SIM | PGM |
|---|---|---|---|---|---|---|---|---|---|
| Ingredients (g/l) | Macro elements | N6 | R2 | R2 | R2 | LS | LS | LS | 1/2 MS |
| | Micro elements | B5 | R2 | R2 | R2 | LS | LS | LS | 1/2 MS |
| | Vitamins | B5 | R2 | R2 | R2 | LS | LS | LS | 1/2 B5 |
| | Sucrose | 30 | | | 30 | 30 | 30 | 40 | 10 |
| | Glucose | | 10 | 10 | | | | | |
| | Agarose Type 1 | | 7 | | 7 | 7 | 7 | 7 | |
| | Phytagel | 2.5 | | | | | | | 2.5 |
| | pH | 5.8 | 5.2 | 5.2 | 6.0 | 5.8 | 5.8 | 5.8 | 5.8 |
| Hormones (mg/l) | 2,4-D | 2.5 | 2.5 | 2.5 | 2.5 | 2.5 | 2.5 | | |
| | IAA | | | | | | | 0.5 | |
| | BAP | | | | | | | 0.3 | |
| | NAA | | | | | | | | 0.05 |
| Additives | Proline (mg/l) | 500 | | | | | | | |
| | Glutamine (mg/l) | 500 | | | | | | | |
| | Casein Enzymatic Hydrolysate (mg/l) | 300 | | | | | | | |
| | Acetosyringone ($\mu$M) | | 100 | 100 | | | | | |
| | Cocosnutwater (ml) | | | | | 100 | 100 | | |
| Antibiotics (mg/l) | Vancomycin | | | | 100 | 100 | 100 | 100 | |
| | Cefotaxime | | | | 400 | 100 | 100 | 100 | |

EXAMPLE 6

Rice Transformation by Particle Gun

Described below is the method used for transformation of non-morphogenic cell suspensions of Oryza sativa cv. IR 52 using a particle inflow gun (PIG) according to Finer et al. (Plant Cell Rep. 11, 323–328, 1992).

A long-term, non-morphogenic suspension culture of Oryza sativa cv. IR 52 was subcultured in weekly intervals in liquid LS-4 (Linsmaier and Skoog, Physiol. Plant. 18, 100–127, 1962) medium and maintained on a rotary shaker (110 rpm) at 28° C. in the dark. (The contents of the LS-4 medium can be found in Table Z). 3–4 days after the last subculture 1.5 ml of this cell suspension (appro. $1.5 \times 10^6$ cells) were evenly spread on a filter paper (Whatman no 4) which was subsequently placed on solidified LS-4 medium and cultivated in the dark at 28° C. for 24 h and directly used for bombardment thereafter. For microprojectile bombardment a home-made particle inflow gun (PIG) according to Finer et al. (1992) was used. 300 $\mu$g tungsten particles coated with either pMOG 617 (35S-gus and 35S-hyg) or pMOG 873 (35S-cah) were loaded on a particle support. The particles were accelerated by a 2.5 bar helium pulse and had to pass a 500 $\mu$m metal stop screen, placed 2 cm under the particle support. The suspension cells were placed 15 cm under the particle support. The PIG was evacuated to 30 mbar before bombardment. After bombardment the cells were cultured at 28° C. in the dark for 3 days. Then the filters with the cells were transferred to solid LS-4 medium containing various concentrations of cyanamide or 50 mg/l hygromycinB (see table 6). The subculture was repeated every 9 days. Resistant microcalli that were visible after 4–6 weeks were transferred to fresh LS-4 medium containing the respective selective agent. From two experiments 7+41 calli of the developing callus for the presence of the DNA in the callitransformed with pMOG873. One of the 4 surviving calli on 40 mg/l cyanamide showed positive in a PCR experiment on the cah-gene.

TABLE 6

Media required for Oryza sativa cv. IR 52 transformation

| | LS-4 liquid | LS-4 solid |
|---|---|---|
| Macro elements | LS | LS |
| Micro elements | LS | LS |
| Vitamins | LS | LS |
| Sucrose (g/l) | 30 | 30 |
| Agarose Type I (g/l) | — | 7 |
| pH | 5.8 | 5.8 |
| 2,4-D (mg/l) | 4 | 4 |

TABLE 7

| Selective agent (mg/l) | Number of plates | resistant clones | gus positive |
|---|---|---|---|
| pMOG617 | | | |
| Cyanamide 20 | 4 | | |
| Cyanamide 30 | 2 | | |
| Cyanamide 40 | 4 | | |
| Cyanamide 50 | 2 | | |
| Cyanamide 60 | 2 | | |
| Cyanamide 70 | 2 | | |
| Cyanamide 80 | 2 | | |
| Hygromycin 50 | 8 | | |
| pMOG 873 | | | |
| Cyanamide 0 | 4 | | |

TABLE 7-continued

| Selective agent (mg/l) | Number of plates | resistant clones | gus positive |
|---|---|---|---|
| Cyanamide 20 | 6 | | |
| Cyanamide 30 | 8 | | |
| Cyanamide 40 | 8 | | |
| Cyanamide 50 | 7 | | |
| Cyanamide 60 | 4 | | |
| Cyanamide 70 | 4 | | |
| Cyanamide 80 | 2 | | |
| Hygromycin 50 | 4 | | |

EXAMPLE 8

Maize Killing Curve

Stock solutions of cyanamide were prepared in water at 10 and 100 mg/ml and filter sterilised. Aliquots were stored at −20° C. Media were prepared by adding MS medium (4.4 g), sucrose (20 g), 2,4-D (2.0 mg) and agar (8 g) to 1 litre of water. After autoclaving the appropriate amount of cyanamide (0, 10, 30, 50, 100, 150 mg/L cyanamide) was added and the media was poured into 9 cm petri dishes. BMS liquid was prepared as above minus agar. BMS cells were added to media containing cyanamide in three ways:

a. BMS cell suspension added to falcon tube and liquid removed. Then the BMS cells were arranged on the surface of the agar in clumps of approximately 5 mm in diameter, 5 clumps per plate, 3 plates per concentration, while on the base of each petri dish the outline of each clump was marked;
b. Approximately 0.5 ml pack cell volume plus 1.5 ml BMS liquid added to surface of agar and the cells were spread finely over surface of agar. Three plates per treatment were set up.
c. Approximately 0.5 ml pack cell volume plus 1.5 ml BMS liquid were added to filter paper overlying agar. Cells were spread evenly over surface of filter. One plate per treatment was set up.

The plates were sealed with micropore tape and incubated at 25° C. in the dark. The growth of the cells was observed after 7 and 14 days.

Results

Day 8

The growth of BMS cells on cyanamide was assessed after 8 days. The clumps of BMS cells arranged on the surface of the control media had increased in size and outgrown their original outline. Cells on 10 mg/l had not outgrown their outline but the height of the clumps had increased forming an uneven surface. A slight reduction of growth with increased cyanamide concentration was apparent with the maximum effect on growth observed at 50 mg/l cyanamid.

The cells which were spread over the surface of the control media had grown well and densely covered the surface of the media. A significant reduction in growth was observed on the lowest level of cyanamide (10 mg/l), however, an increased cell density was clearly visible. A slight increase in cell density was evident on 30 mg/l cyanamid, but it was difficult to distinguish different growth rates on higher concentrations.

Cells on all levels of cyanamide remained a milky white colour, no browning of cells was observed.

Day 15 (Table 9)

The reduction in growth of BMS cells on 10 mg/l was still very clear after 15 days on cyanamide, however, the cells arranged in clumps had outgrown their original outline. Cells spread directly over the surface of the agar showed a similar response to those arranged in clumps with a notable reduction in growth observed on 30 mg/l plus. Cells on 50 mg/l plus showed no signs of growth and the surface of the clumps remained very flat but the cells were still milky white in colour. A similar response was observed with cell spread over a filter. However, small raised lumps were observed on the surface on all filters but these did not develop further into colonies and were evidently comprised of the larger cell aggregates from a mixed population of sizes typical in BMS suspensions.

Samples were taken from the clumps of cells on all levels of cyanamide for observation under a light microscope. With increasing levels of cyanamide there were increasing numbers of dead cells where the cell contents had shrunk away from the cell wall, and an increase in the number of dark bodied starch grains. Cells were observed resuspended in water and with FDA stain under UV light.

TABLE 9

| Cynamide Level (mg/l) | Observations |
|---|---|
| 0 | Normal healthy cells with occasional dead cells. |
| 10 | Signs of stress. Odd clump of dead cells amongst healthy cells. Approx 5% dead. |
| 30 | Striking differences from control cells. Accumulation of starch grains. Dead cells with cell contents shrunk away from cell wall. Approx 15–20% dead. |
| 50 | Quite different to 30. Increasing number of dead cells and accumulation of starch grains. Approx 50% dead. |
| 100 | Majority of cell dead. Small clear spherical objects possibly oil droplets accumulating in cells. Cells decreasing in size. Approx 90% dead. |
| 150 | Majority of cells dead. Cells appear darker in colour due to accumulation of starch grains and phenols. Odd living cell visibie in clump of dead cells. Approx 95–98% dead. |

The Experiment was repeated with cyanamide concentrations of 0, 10, 20, 30, 40, 50, 60, 70, 80, 90 and 100 mg/l cyanamid. The results were similar to those described above, i.e. for the cells aggregated in climps a slight reduction in growth was seen at 10 mg/l. From a concentration of 20 mg/l cyanamide on the cell clumps showed no outgrowing from their original outline, but at the lower concentrations (<50 mg/l ) the cell clumps showed an increase in height (decreasing with higher concentrations). Above 50 mg/l the clumps showed a slight orange tinge.

The result with cells spread over the surface of the agar or on the filters were similar in that at a concentration of 10 mg/l showed a slight growth (approximately doubling of the number of original cells), while at concentrations of 20 mg/l and higher exhibited limited of growth.

EXAMPLE 8

Kill Curves in Banana (Musa)

To test the potential of cyanamide as a selection agent for transformation in banana two kill curves were set up with a regenerable embryogenic suspension of Grand nain 6 day old embryogenic suspension (Ed6b) cultures, subbed routinely in M2 2,4D liquid, containing 4.32 g/l MS salts, 45 g/l sucrose, standard 1×concn. MS vitamins, 100mg/l glutamine, 100 mg/l myo-inositol, 100 mg/l biotin, 100mg/l malt extract at pH 5.3 and added after autoclaving 1.2 mg/l 2,4-D and 0.8 mg/l picloram.

Cultures were sieved (>250μ, <710μ) and aliquots of approx 50 μl sieved culture in 300μl volume of liquid were pipetted onto two kill curve media as detailed below (3 reps per plate). Culture growth and survival were monitored over the following 3 weeks and cell survival assessed after 21 days via FDA staining.

Kill Curve Medium A : M2/MS/1.0 2,4-D (as M2/MS/2,4-D except only 1.0 mg/l 2,4-D, no picloram and +2.25 g/l gelrite): this medium promotes the rapid division and growth of embryogenic callus, but not embryos. Kill Curve Medium B : M2/SH/0.5Pic, 0.5 2,4-D (as M2/MS/2,4-D except only 0.5 mg/l 2,4-D and 0.5 mg/l picloram, SH salts (4.32 g/1) instead of MS, +2.25 g/l gelrite): This medium promotes the early development of embryos which can be matured and germinated by transfer to alternative media.

Cyanamide was added to both media types, after autoclaving, to concentrations of 0,20,30,50,75,100,150 mg/l.

The results are depicted in Table 10, where the figures on cell growth are approximate visual estimates, not precise measurements of callus volume. There is no significant visual browning of cultures and release of phenolics until concentrations of >75 mg/l. Generally cultures just stop growing, with cell division being widely inhibited. Cyanamide inhibits the growth of embryogenic callus by 40–50% at even low concentrations of 20 mg/l, without causing significant visual damage. Embryogenesis was totally inhibited at the lowest concentration tested here.

TABLE 10

Results of cyanamide concentrations on banana cell culture.

| Medium | Cyanamide Concentration | % Live cells as assessed by FDA | Embryos Formed (average) | % Callus Growth |
|---|---|---|---|---|
| M2/MS/2,4-D | 0 | 95% | N/A | +100% |
| M2/MS/2,4-D | 20 | 60% | N/A | +30% |
| M2/MS/2,4-D | 30 | 50% | N/A | +20% |
| M2/MS/2,4-D | 50 | 20% | N/A | 0 |
| M2/MS/2,4-D | 75 | 10% | N/A | 0 |
| M2/MS/2,4-D | 100 | 10% | N/A | 0 |
| M2/MS/2,4-D | 150 | 0 | N/A | 0 |
| M2/SH/0.5Pic +0.5 2,4-D | 0 | 95% | 51 | N/A |
| M2/SH/0.5Pic +0.5 2,4-D | 20 | 50% | 0 | N/A |
| M2/SH/0.5Pic +0.5 2,4-D | 30 | 40% | 0 | N/A |
| M2/SH/0.5Pic +0.5 2,4-D | 50 | 30% | 0 | N/A |
| M2/SH/0.5Pic +0.5 2,4-D | 75 | 20% | 0 | N/A |
| M2/SH/0.5Pic +0.5 2,4-D | 100 | 10% | 0 | N/A |
| M2/SH/0.5Pic +0.5 2,4-D | 150 | 0 | 0 | N/A |

What is claimed is:

1. A method for selecting transformed monocotyledonous plant cells, plant tissue, or plant parts, the method comprising:
   (a) obtaining a vector comprising a coding sequence for cyanamide hydratase and a coding sequence for a gene of interest, said coding sequence for cyanamide hydratase comprising SEQ ID NO:1;
   (b) transforming monocotyledonous plant cells with said vector; and
   (c) selecting monocotyledonous plant cells, plant tissues, or plant parts comprising transformed monoctyledonous plant cells that are tolerant to cyanamide in a tissue culture medium comprising cyanamide.

2. A method for selecting tranformed plant cells, comprising:
   (a) tranforming plant cells with a vector comprising a nucleic acid sequence coding for cyanamide hydratase, said nucleic acid sequence comprising SEQ ID NO:1;
   (b) growing said plant cells or progeny of said plant cells in a tissue culture medium comprising cyanamide; and
   (c) selecting transformed plant cells which survive exposure to said cyanamide.

3. The method of claim 2, wherein said cells are plant cells.

4. A method for selecting transformed monocotyledonous plant cells, plant tissue, or plant parts, the method comprising:
   (a) growing monocotyledonous plant cells, plant tissue, or plant parts comprising a nucleic acid sequence of SEQ ID NO:1 in a medium comprising cyanamide; and
   (b) selecting transformed plant cells, plant tissue, or plant parts which survive exposure to said cyanamide.

5. A transgenic monocotyledonous plant comprising a nucleotide sequence coding for cyanamide hydratase and a nucleotide sequence coding for a gene of interest, wherein said nucleotide sequence coding for cyanamide hydratase is used as a selectable marker and comprises SEQ ID NO:1.

6. A method for selecting transformed dicotyledonous plant cells, plant tissue, or plant parts, the method comprising:
   (a) obtaining a vector comprising a coding squence for cyanamide hydratase and a coding sequence for a gene or interest;
   (b) transforming dicotyledonous plant cells with said vector; and
   (c) selecting dicotyledonous plant cells, plant tissue, or plant parts comprising transformed dicotyledonous plant cells that are tolerant to cyanamide in a tissue culture medium comprising cyanamide;

wherein said coding sequence for cyanamide hydratase is used as a selectable marker and comprises SEQ ID NO:1.

7. The method according to claim 6, wherein the dicotyledonous plant cells are selected from the group consisting of potato cells, tomato cells, and Arabidopsis cells.

8. The method according to claim 1, wherein the monocotyledonous plant cells are selected from the group consisting of rice cells, maize cells, banana cells, and wheat cells.

9. The method according to claim 7, wherein the dicotyledonous plant cells are potato cells.

10. The method according to claim 8, wherein the monocotyledonous plant cells are rice cells.

11. The method according to claim 8, wherein the monocotyledonous plant cells are wheat cells.

12. The method according to claim 8, wherein the monocotyledonous plant cells are banana cells.

13. Transgenic plant cells, plant tissue, or plant parts selected according to the method of claim 1.

14. A method for selecting transformed dicotyledonous plant cells, plant tissue, or plant parts, the method comprising:

(a) growing dicotyledonous plant cells, plant tissue, or plant parts transformed with a nucleic acid sequence comprising SEQ ID NO:1 in a medium comprising cyanamide; and (b) selecting transformed plant cells, plant tissue, or plant parts which survive exposure to said cyanamide.

15. A transgenic dicotyledonous plant comprising a nucleotide sequence coding for cyanamide hydratase and a nucleotide sequence coding for a gene of interest, wherein said nucleotide sequence coding for cyanamide hydratase is used as a selectable marker and comprises SEQ ID NO:1.

16. A transgenic plant regenerated from plant cells obtained by the method of claim 3.

17. The method of claim 2, wherein said vector further comprises a coding sequence for a gene of interest.

18. The method of claim 4, wherein said nucleic acid further comprises a coding sequence for a gene of interest.

19. The method of claim 14, wherein said nucleic acid further comprises a coding sequence for a gene of interest.

* * * * *